(12) United States Patent
Chiba et al.

(10) Patent No.: US 11,193,899 B2
(45) Date of Patent: Dec. 7, 2021

(54) NON-DESTRUCTIVE METHOD FOR EVALUATING STRUCTURE OF WATER-ABSORBING RESIN

(71) Applicant: SUMITOMO SEIKA CHEMICALS CO., LTD., Hyogo (JP)

(72) Inventors: Mikito Chiba, Himeji (JP); Yuichi Onoda, Himeji (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 41 days.

(21) Appl. No.: 16/490,038

(22) PCT Filed: Mar. 2, 2018

(86) PCT No.: PCT/JP2018/007963
§ 371 (c)(1),
(2) Date: Aug. 29, 2019

(87) PCT Pub. No.: WO2018/159804
PCT Pub. Date: Sep. 7, 2018

(65) Prior Publication Data
US 2020/0326288 A1 Oct. 15, 2020

(30) Foreign Application Priority Data
Mar. 2, 2017 (JP) .............................. JP2017-038983

(51) Int. Cl.
*G06K 9/00* (2006.01)
*C08F 2/00* (2006.01)
(Continued)

(52) U.S. Cl.
CPC ........... *G01N 23/046* (2013.01); *G01B 15/00* (2013.01); *G01N 23/083* (2013.01);
(Continued)

(58) Field of Classification Search
USPC ........ 382/100, 103, 108–109, 123, 131–132, 382/154, 168, 173, 181, 189, 206, 219,
(Continued)

(56) References Cited

U.S. PATENT DOCUMENTS

| 5,180,798 A * | 1/1993 | Nakamura ................ C08F 2/32 |
| | | 526/66 |
| 2003/0147490 A1 * | 8/2003 | Stabe ................... G01N 23/046 |
| | | 378/4 |

(Continued)

FOREIGN PATENT DOCUMENTS

| JP | H03-227301 A | 10/1991 |
| JP | 2007-154350 A | 6/2007 |

(Continued)

OTHER PUBLICATIONS

Extended European Search Report in European Patent Application No. 18761563.8 dated Feb. 2, 2021.
(Continued)

*Primary Examiner* — Seyed H Azarian
(74) *Attorney, Agent, or Firm* — Knobbe, Martens, Olson & Bear, LLP

(57) ABSTRACT

Provided is a non-destructive method for evaluating the structure of a water-absorbing resin which can be advantageously used for controlling various properties of the water-absorbing resin. This non-destructive method for evaluating the structure of a water-absorbing resin involves non-destructively evaluating the structure of a water-absorbing resin through an X-ray computer tomographic technique, wherein the method comprises a step 1 for installing the water-absorbing resin to be evaluated on a test piece stage of an X-ray computer tomography device, a step 2 for performing X-ray computer tomography on the water-absorbing resin using the X-ray computer tomography device and acquiring tomographic image data of the water-absorbing
(Continued)

resin, and a step 3 for analyzing the tomographic image data using image analysis software and obtaining a tomographic image of the water-absorbing resin.

6 Claims, 1 Drawing Sheet

(51) Int. Cl.
  *G01N 23/046* (2018.01)
  *G06T 7/62* (2017.01)
  *G01B 15/00* (2006.01)
  *G01N 23/083* (2018.01)
  *G06T 7/00* (2017.01)
  *G06T 11/00* (2006.01)

(52) U.S. Cl.
  CPC .............. *G06T 7/0004* (2013.01); *G06T 7/62* (2017.01); *G06T 11/003* (2013.01); *G01N 2223/401* (2013.01); *G06T 2207/10081* (2013.01); *G06T 2207/30108* (2013.01)

(58) Field of Classification Search
  USPC ....... 382/254, 276, 286, 305, 320, 141, 243; 378/4; 523/115; 526/66; 604/367; 264/113
  See application file for complete search history.

(56) References Cited

U.S. PATENT DOCUMENTS

| | | | | |
|---|---|---|---|---|
| 2007/0264489 A1* | 11/2007 | Sasabe | ............... | C08J 3/248 428/327 |
| 2012/0018915 A1* | 1/2012 | Ookubo | ............... | B33Y 10/00 264/113 |
| 2014/0213687 A1* | 7/2014 | Yamazaki | ............. | C08F 292/00 523/115 |
| 2015/0223999 A1* | 8/2015 | Goda | ............... | A61F 13/15634 604/367 |
| 2019/0359358 A1* | 11/2019 | Torii | ............... | B01J 20/28011 |
| 2020/0086283 A1* | 3/2020 | Tezuka | ............... | B01D 67/0086 |

FOREIGN PATENT DOCUMENTS

| | | |
|---|---|---|
| JP | 2014-090749 A | 5/2014 |
| JP | 2016-150949 A | 8/2016 |

OTHER PUBLICATIONS

Hokoci, H., "Industrial X-ray Inspection System, Observations of Superabsorbent Polymers Using the inspeXio SMX-100CT Microfocus X-Ray CT System," Shimadzu Excellende in Science, Application News No. N121, May 1, 2013, in 2 pages.

International Search Report for International Application No. PCT/JP2018/007963, dated Apr. 24, 2018 (in 1 page).

* cited by examiner

NON-DESTRUCTIVE METHOD FOR EVALUATING STRUCTURE OF WATER-ABSORBING RESIN

TECHNICAL FIELD

The present invention relates to a non-destructive method for evaluating a structure of a water-absorbent resin; more particularly, the present invention relates to a method for non-destructive evaluation of the structure of the water-absorbent resin through X-ray computed tomography and a method for screening a water-absorbent resin used for an absorbent material.

BACKGROUND ART

A water-absorbent resin is widely used in a field of an absorbent article including hygienic materials such as disposable diapers and sanitary napkins; agricultural and horticultural materials such as a water-retention material and a soil conditioner; and industrial materials such as a water blocking material and a dew condensation prevention material (see Patent Document 1).

In recent years, in the field of a wide variety of water-absorbent resins, physical properties of the water-absorbent resins are required to be controlled in accordance with the needs. Examples of the physical properties of the water-absorbent resin include water-absorption rate, centrifuge retention capacity, saline flow conductivity, absorbency under pressure, and mass average particle diameter. Examples of methods of controlling these various physical properties include surface crosslinking treatment of a water-absorbent resin, adjustment of particle shape and particle size distribution, and adjustment of specific surface area and internal structure of particles.

PRIOR ART DOCUMENT

Patent Document

Patent Document 1: Japanese Patent Laid-open Publication No. H3-227301

SUMMARY OF THE INVENTION

Problems to be Solved by the Invention

Visualizing and observing the appearance and interior of the water-absorbent resin as an indicator of the physical properties of the water-absorbent resin is considered to be one of useful methods. As a method of observing the water-absorbent resin, there is a method of observing the water-absorbent resin with an optical microscope, a scanning electron microscope or the like. However, these means cannot observe the interior of the water-absorbent resin. As a method of observing the interior of the water-absorbent resin, a cross-section of the water-absorbent resin directly broken by a crusher or the like in advance can be observed by the above-mentioned observation method; however, there are problems that the work is complicated and it is difficult to obtain reproducibility because the crushed cross-section is observed.

Under such circumstances, a main object of the present invention is to provide a non-destructive method for evaluating a structure of a water-absorbent resin which can be advantageously used for controlling various properties of the water-absorbent resin.

Means for Solving the Problem

The inventors of the present invention conducted a diligent study to solve the aforementioned problem. As a result, the inventors have found a method for non-destructive evaluation of a structure of a water-absorbent resin through X-ray computed tomography. It has been found that the non-destructive method for evaluating a structure of a water-absorbent resin, including a step 1 of placing the water-absorbent resin to be evaluated on a sample stage of an X-ray computer tomography apparatus, a step 2 of performing X-ray computer tomography on the water-absorbent resin by using the X-ray computer tomography apparatus to acquire tomographic image data of the water-absorbent resin, and a step 3 of analyzing the tomographic image data by using image analysis software to obtain a cross-sectional image of the water-absorbent resin can be advantageously used for controlling various properties of the water-absorbent resin based on the evaluated structure. In particular, it has been found that a cavity area ratio of the water-absorbent resin evaluated by the non-destructive evaluation method is largely related to a liquid-retention capacity under a load and an amount of re-wet in water absorbed by the water-absorbent resin, and it has been clarified that various properties of the water-absorbent resin can be suitably controlled by controlling the cavity area ratio.

The present invention has been accomplished as a result of further study based on these findings.

In summary, the present invention provides aspects of the invention comprising the following features:

Item 1. A non-destructive method for evaluating a structure of a water-absorbent resin through X-ray computed tomography, the method including a step 1 of placing the water-absorbent resin to be evaluated on a sample stage of an X-ray computer tomography apparatus, a step 2 of performing X-ray computer tomography on the water-absorbent resin by using the X-ray computer tomography apparatus to acquire tomographic image data of the water-absorbent resin, and a step 3 of analyzing the tomographic image data by using image analysis software to obtain a cross-sectional image of the water-absorbent resin.

Item 2. The non-destructive method for evaluating a structure of a water-absorbent resin, according to item 1, further including a step 4a of, by using image processing software, measuring a total cross-sectional area (A) of resin portions in the water-absorbent resin and a total cross-sectional area (B) of cavity portions in the water-absorbent resin from the cross-sectional image of the water-absorbent resin and a step 5 of calculating a cavity area ratio of the water-absorbent resin by Evaluation (I):

cavity area ratio [%]={total cross-sectional area ($B$) of cavity portions in the water-absorbent resin/ (total cross-sectional area ($A$) of resin portions in the water-absorbent resin+total cross-sectional area ($B$) of cavity portions in the water-absorbent resin)}×100.　　(I)

Item 3. The non-destructive method for evaluating a structure of a water-absorbent resin, according to item 1, further including a step 4b-1 of, by using image processing software, measuring a total cross-sectional area (A) of resin portions in the water-absorbent resin and a cross-sectional area (C) of a cross section of the water-absorbent resin in which cavities are filled from the cross-sectional image of the water-absorbent resin, a step 4b-2 of subtracting the total cross-sectional area (A) from the cross-sectional area (C) to calculate the total cross-sectional area (B) of cavity portions in the water-absorbent resin, and a step 5 of calculating a cavity area ratio of the water-absorbent resin by Equation (I):

cavity area ratio [%]={total cross-sectional area (B) of cavity portions in the water-absorbent resin/ (total cross-sectional area (A) of resin portions in the water-absorbent resin+total cross-sectional area (B) of cavity portions in the water-absorbent resin)}×100. (I)

Item 4. The non-destructive method for evaluating a structure of a water-absorbent resin, according to any one of items 1 to 3, wherein the shape of the water-absorbent resin to be evaluated is a granular shape, a substantially spherical shape, a crushed indefinite shape, a flat shape, a shape in which particles having a substantially spherical shape are aggregated, or a shape in which particles having a crushed indefinite shape are aggregated.

Item 5. A method for screening a water-absorbent resin used for an absorbent material, including nondestructively evaluating a structure of the water-absorbent resin by a method including a step 1 of placing the water-absorbent resin to be evaluated on a sample stage of an X-ray computer tomography apparatus, a step 2 of performing X-ray computer tomography on the water-absorbent resin by using the X-ray computer tomography apparatus to acquire tomographic image data of the water-absorbent resin, and a step 3 of analyzing the tomographic image data by using image analysis software to obtain a cross-sectional image of the water-absorbent resin, and selecting the water-absorbent resin to be used for the absorbent material.

Advantages of the Invention

The present invention can provide the non-destructive method for evaluating a structure of a water-absorbent resin which can be advantageously used for controlling various properties of the water-absorbent resin.

EMBODIMENTS OF THE INVENTION

Figure 1:
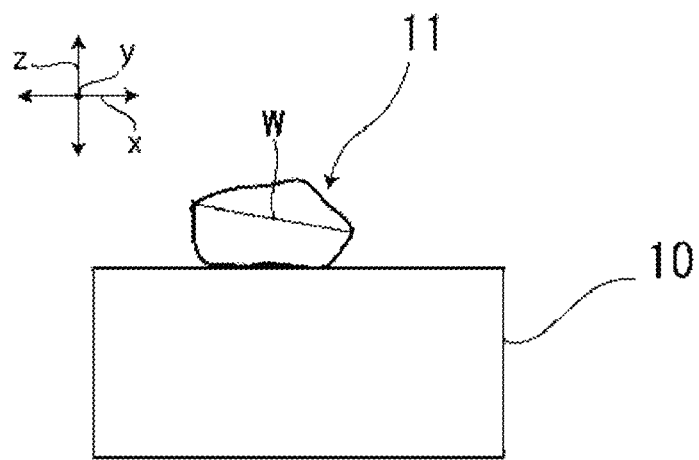
FIG. 1 is a schematic diagram for use in illustrating a method for measuring the cavity area ratio of a water-absorbent resin using X-ray computed tomography.

A non-destructive method for evaluating a structure of a water-absorbent resin of the present invention is a method for non-destructive evaluation of the structure of the water-absorbent resin through X-ray computed tomography and includes the following steps 1 to 3.

Step 1: The water-absorbent resin to be evaluated is placed on a sample stage of an X-ray computer tomography apparatus.

Step 2: X-ray computer tomography is performed on the water-absorbent resin by using the X-ray computer tomography apparatus to acquire tomographic image data of the water-absorbent resin.

Step 3: The tomographic image data is analyzed using image analysis software to obtain a cross-sectional image of the water-absorbent resin.

The non-destructive method for evaluating a structure of a water-absorbent resin of the present invention will be hereinafter described in detail.

(Step 1)

In the non-destructive evaluation method of the present invention, the step 1 is a step of placing the water-absorbent resin to be evaluated on the sample stage of the X-ray computer tomography apparatus.

The X-ray computer tomography apparatus is not particularly limited, and a commercially available product can be suitably used. The water-absorbent resin to be evaluated is not particularly limited, and a known water-absorbent resin may be evaluated, or a novel water-absorbent resin may be evaluated. Examples of the water-absorbent resin include a water-absorbent resin formed from a polymer of a water-soluble ethylenically unsaturated monomer.

The size of the water-absorbent resin to be evaluated is not particularly limited. For example, a water-absorbent resin having a median particle diameter of 200 to 600 μm can be used as a suitable evaluation target. The median particle diameter of the water-absorbent resin can be measured using JIS standard sieves. More specifically, the median particle diameter represents a value as measured using the method described in the Examples.

The shape of the water-absorbent resin is not particularly limited, and examples thereof include a granular shape, a substantially spherical shape, a shape in which particles having a substantially spherical shape are aggregated, a crushed indefinite shape, a shape in which particles having a crushed indefinite shape are aggregated, and a flat shape. Through the use of reversed phase suspension polymerization or spray droplet polymerization, a water-absorbent resin having a substantially spherical particle shape, such as a granular shape, a spherical or elliptical shape, or a shape in which particles having a substantially spherical shape are aggregated, can be produced. Through the use of aqueous solution polymerization, a water-absorbent resin having a crushed indefinite shape or a shape in which particles having a crushed indefinite shape are aggregated can be produced. From the viewpoint of controlling a cavity area ratio (a ratio of an area of cavity portions in the cross-sectional image) described later, preferred as the shape of the water-absorbent resin is a granular shape, a substantially spherical shape, or a shape in which particles having a substantially spherical shape are aggregated.

The water-absorbent resin may contain additives suitable for its purpose. Examples of such additives include inorganic powders, surfactants, oxidizing agents, reducing agents, metal chelating agents, radical chain inhibitors, antioxidants, anti-bacterial agents, and deodorizers.

As a more specific method of the step 1, for example, the following method may be mentioned. First, particles of the water-absorbent resin are classified in advance with JIS standard sieves. A plurality of particles are randomly selected from particles of the water-absorbent resin on a sieve with a mesh size of 180 μm that pass through a sieve with a mesh size of 600 μm, and these particles are used as resin samples. Then, each resin sample is placed on the sample stage of the X-ray computer tomography apparatus.

(Step 2)

In the non-destructive evaluation method of the present invention, the step 2 is a step of performing X-ray computer tomography on the water-absorbent resin to be evaluated, using the X-ray computer tomography apparatus to acquire tomographic image data of the water-absorbent resin.

A known method can be adopted as the step of performing X-ray computer tomography on the water-absorbent resin by using the X-ray computer tomography apparatus to acquire tomographic image data of the water-absorbent resin.

(Step 3)

In the non-destructive evaluation method of the present invention, the step 3 is a step of analyzing the tomographic image data obtained in the step 2 using image analysis software to obtain a cross-sectional image of the water-absorbent resin.

The interior of the water-absorbent resin is visualized with the cross-sectional image of the water-absorbent resin, and the structure of the water-absorbent resin can be suitably observed. The evaluation of the structure of the water-absorbent resin can be advantageously used for controlling various properties of the water-absorbent resin.

For example, the use of the non-destructive evaluation method of the present invention makes it possible to calculate the cavity area ratio of the water-absorbent resin (the ratio of the area of cavity portions in the cross-sectional image). Various physical properties of the water-absorbent resin can be suitably controlled based on the cavity area ratio.

More specifically, for the resin sample placed on the sample stage of the X-ray computer tomography apparatus in the step 1, cross-sectional image data is acquired by X-ray computer tomography in the step 2. Next, for the tomographic image data obtained in the step 2, in the step 3, shapes at given angles or given horizontal and vertical cross sections of the resin sample are observed using the image analysis software. Examples of the image analysis software include commercially available products. Such mixtures can be suitably used.

Figure 2:
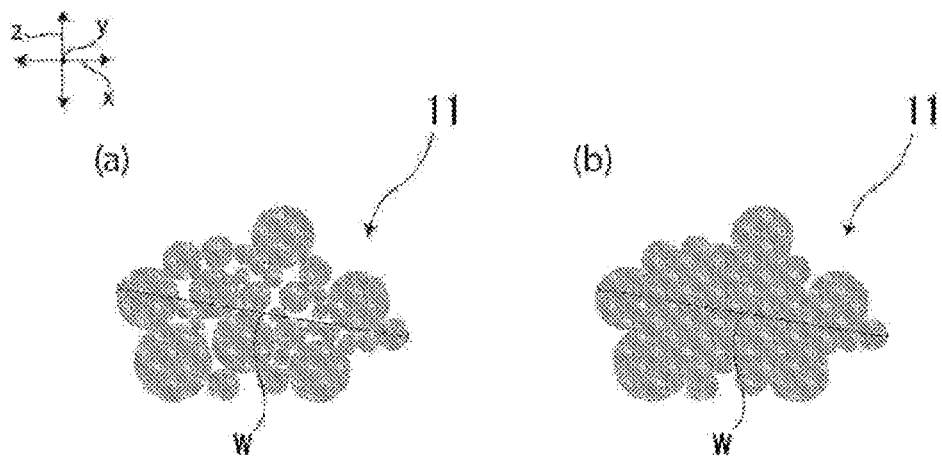
FIG. 2(a) is a schematic diagram of a cross-sectional image of a water-absorbent resin taken using X-ray computed tomography.
FIG. 2(b) is a schematic diagram prepared by filling the cavity portions of FIG. 2(a).

Here, for example, when the cavity area ratio described later is calculated, from given cross sections in horizontal directions (x- and y-directions) and a vertical direction (z-direction) with respect to the mounting surface of the sample stage, a horizontal or vertical cross-sectional image having a maximum distance between given two points on the contour of each of the resin samples is selected. Specifically, as shown in the schematic diagram of FIG. 1, for each of the three directions, x-, y-, and z-directions, that are perpendicular to one another, cross-sectional images of a resin sample 11 on a sample stage 10 are acquired first. Subsequently, for each of these directions, one cross-sectional image having the longest particle length w (see FIGS. 1 and 2) of the resin sample (i.e., a cross-sectional image taken in a position where the particle length of the resin sample is the longest) is selected. Then, a cross-sectional image having the longest particle length w of the resin sample of these three cross-sectional images is selected.

More specifically, initially, cross sections (z-x sections) of slices of the resin sample are observed in y-direction while shifting the position in y-direction with respect to the mounting surface of the sample stage, and a z-x cross section having the longest particle length w of the resin sample (see FIGS. 1 and 2) is acquired. Similarly, cross sections (a z-y cross section and an x-y cross section) having the longest particle length w of the resin sample as observed in x- and z-directions are acquired. Then, a cross section having the longest particle length w of the resin sample of these three cross sections is selected.

The cavity area ratio of the water-absorbent resin can be calculated, for example, by the following step 4a subsequent to the step 3 and the step 5, or the steps 4b-1, 4b-2, and 5.

Step 4a: By using image processing software, a total cross-sectional area (A) of resin portions in the water-absorbent resin and a total cross-sectional area (B) of cavity portions in the water-absorbent resin are measured from the cross-sectional image of the water-absorbent resin obtained in the step 3.

Step 4b-1: By using image processing software, the total cross-sectional area (A) of resin portions in the water-absorbent resin and a cross-sectional area (C) of the cross section of the water-absorbent resin in which cavities are filled are measured from the cross-sectional image of the water-absorbent resin obtained in the step 3.

Step 4b-2: The total cross-sectional area (B) of cavity portions in the water-absorbent resin is calculated by subtracting the total cross-sectional area (A) from the cross-sectional area (C) obtained in the step 4b-1.

Step 5: The cavity area ratio of the water-absorbent resin is calculated by Equation (I):

$$\text{cavity area ratio [\%]} = \{\text{total cross-sectional area } (B) \text{ of cavity portions in the water-absorbent resin} / (\text{total cross-sectional area } (A) \text{ of resin portions in the water-absorbent resin} + \text{total cross-sectional area } (B) \text{ of cavity portions in the water-absorbent resin})\} \times 100. \qquad (I)$$

That is, in the step 4a, for the cross-sectional image obtained in the step 3, by means of the image processing software, the cross-sectional area of the resin sample (the total cross-sectional area (A) of resin portions in the water-absorbent resin) (the area of the filled portions in the schematic diagram of FIG. 2(a)) and the cross-sectional area of cavity portions in the resin sample (the total cross-sectional area (B) of cavity portions in the water-absorbent resin) (the area of uncolored blank portions surrounded by the filled portions in the schematic diagram of FIG. 2(a)) are measured. In image processing in this case, for example, a region having a lightness greater than an arbitrary threshold can be taken as the total cross-sectional area (A) of resin portions in the water-absorbent resin, and a region having a lightness lower than the arbitrary threshold in a region surrounded by the filled portion can be taken as the total cross-sectional area (B) of cavity portions in the water-absorbent resin.

In the step 4b-1, for the cross-sectional image obtained in the step 3, by means of the image processing software, the cross-sectional area of the resin sample (the total cross-sectional area (A) of resin portions in the water-absorbent resin) (the area of the filled portions in the schematic diagram of FIG. 2(a)) and the cross-sectional area (C) of the cross section of the resin sample in which cavities are filled (the area of the filled portion in the schematic diagram of FIG. 2(b)) are measured. In the step 4b-2, the cross-sectional area of cavity portions in the resin sample (the total cross-sectional area (B) of cavity portions in the water-absorbent resin) is calculated by subtracting the cross-sectional area (A) of the resin sample from the cross-sectional area (C) of the resin sample in which cavities are filled.

In the step 5, the cavity area ratio of the resin sample is calculated by Equation (I) above. Using this method, the cavity area ratio of the resin sample is measured for each of the resin samples, and the average value thereof is determined as the cavity area ratio of the water-absorbent resin.

The phrase "total cross-sectional area (A) of resin portions in the water-absorbent resin" refers to the total cross-sectional area of portions where the water-absorbent resin is present (filled portions) in the cross-sectional image of the water-absorbent resin, as shown in the schematic diagram of FIG. 2(a), for example. The phrase "total cross-sectional area (B) of cavity portions in the water-absorbent resin" refers to the total area of cavity portions in the water-absorbent resin (blank portions in the water-absorbent resin) in the cross-sectional image of the water-absorbent resin, as shown in the schematic diagram of FIG. 2(a), for example.

As described above, when the cavity area ratio of the water-absorbent resin is calculated, it is preferable to select a cross-sectional image having the longest particle length w of the resin sample in the step 3 prior to the steps 4a and 5 or the steps 4b-1, 4b-2, and 5.

Specific examples of conditions for X-ray computer tomography were as follows:
Apparatus: MicroXCT-400 (Xradia Inc.)
X-ray tube voltage: 80 kV
X-ray tube current: 122 μA
Optical lens: 10 times
Irradiation time: 0.8 sec
Pixel size: 2.149 μm
X-ray source-to-sample distance: 29.1533 mm
Detector-to-sample distance: 7.3723 mm
Imaging range: −90° to 90°
Image analyzer: myVGL 2.2 (Volume Graphics GmbH)

For example, when the cavity area ratio calculated by the non-destructive evaluation method of the present invention is 10% or less, a water-absorbent resin that exhibits a high liquid-retention capacity under a load and has a small amount of re-wet can be achieved. It is believed that the amount of the liquid retained in cavity portions (gap portions) of the water-absorbent resin is small, such that the liquid is favorably absorbed by the water-absorbent resin, and as a result, the water-absorbent resin exhibits a high liquid-retention capacity under a load, and effectively reduces the amount of re-wet from the cavity portions.

The cavity area ratio of the water-absorbent resin is measured by the non-destructive evaluation method of the present invention, and the structure of the water-absorbent resin is designed based on the cavity area ratio, whereby various physical properties of the water-absorbent resin can be controlled. The cavity area ratio of the water-absorbent resin can be adjusted by suitably setting production conditions of the water-absorbent resin.

For example, when the water-absorbent resin is formed from a polymer of a water-soluble ethylenically unsaturated monomer, to polymerize the water-soluble ethylenically unsaturated monomer, a representative polymerization method such as aqueous solution polymerization, spray droplet polymerization, emulsion polymerization, or reversed phase suspension polymerization is used. In aqueous solution polymerization, polymerization is performed by heating, optionally with stirring, an aqueous solution of the water-soluble ethylenically unsaturated monomer. Examples of methods for controlling the cavity area ratio in aqueous solution polymerization include a method in which a foaming agent, for example, is added to the water-soluble ethylenically unsaturated monomer; and a method in which particles of a water-absorbent resin obtained by aqueous solution polymerization are aggregated. In reversed phase suspension polymerization, polymerization is performed by heating the water-soluble ethylenically unsaturated monomer with stirring in a hydrocarbon dispersion medium. Examples of methods for controlling the cavity area ratio in reversed phase suspension polymerization include a method in which a foaming agent, for example, is added to the first-stage water-soluble ethylenically unsaturated monomer; a method in which the median particle diameter of primary particles obtained in the first-stage reversed phase suspension polymerization is controlled; and a method in which a hydrous gel obtained after the first-stage polymerization is further heated.

A water-absorbent resin is widely used in a field of an absorbent article including hygienic materials such as disposable diapers and sanitary napkins; agricultural and horticultural materials such as a water-retention material and a soil conditioner; and industrial materials such as a water blocking material and a dew condensation prevention material. For example, in hygienic materials such as disposable diapers and sanitary napkins, the water-absorbent resin constitutes an absorbent material and is suitably used for an absorbent article including the absorbent material. The structure of the water-absorbent resin used for an absorbent material is evaluated by the non-destructive evaluation method of the present invention, whereby the water-absorbent resin suitably used for the absorbent material can be screened.

Specifically, in the method for screening a water-absorbent resin of the present invention, the structure of the water-absorbent resin is nondestructively evaluated by the method including the steps 1 to 3 described above, and the water-absorbent resin to be used for an absorbent material is selected. When the cavity area ratio is to be calculated, for example, the steps 4a and 5, or the steps 4b-1, 4b-2, and 5 are further performed to select a water-absorbent resin to be used for the absorbent material.

For example, when a water-absorbent resin having a cavity area ratio of 10% or less is selected by the screening method, it is possible to select a water-absorbent resin with a small amount of re-wet and apply the water-absorbent resin to an absorbent material.

The absorbent material including the water-absorbent resin is composed of, for example, the water-absorbent resin and hydrophilic fibers. Examples of structures of the absorbent material include a mixed dispersion obtained by mixing the water-absorbent resin and hydrophilic fibers to give a homogeneous composition; a sandwich structure in which the water-absorbent resin is sandwiched between layered hydrophilic fibers; and a structure in which the water-absorbent resin and hydrophilic fibers are wrapped in tissue paper. The absorbent material may also contain other components such as thermally fusible synthetic fibers for enhancing the shape retention properties of the absorbent material, a hot melt adhesive, and an adhesive binder such as an adhesive emulsion. For example, a water-absorbent resin evaluated to have a cavity area ratio of 10% or less by the method for screening a water-absorbent resin of the present invention exhibits a high liquid-retention capacity under a load even when used for an absorbent material having a small proportion of hydrophilic fibers, and has a small amount of re-wet, and therefore, for example, the water-absorbent resin can be used for an absorbent material substantially free of hydrophilic fibers (ie, the content of hydrophilic fibers in the absorbent material is 0% by mass). Examples of absorbent materials substantially free of hydrophilic fibers include water-absorbent sheets.

The content of the water-absorbent resin in the absorbent material may be 50% by mass or more or 70 to 100% by mass.

Examples of hydrophilic fibers include cellulose fibers such as cotton-like pulp made from wood, mechanical pulp, chemical pulp, and semi-chemical pulp; artificial cellulose fibers such as rayon and acetate; and fibers made of synthetic resins such as hydrophilized polyamide, polyester, and polyolefin.

The absorbent material including the water-absorbent resin can be held between a liquid-permeable sheet (top sheet) that allows a liquid to pass through and a liquid-impermeable sheet (back sheet) that does not allow a liquid to pass through, to obtain an absorbent article. The liquid-permeable sheet is positioned on the side of the absorbent article that is brought into contact with the body, and the liquid-impermeable sheet is positioned opposite to the side that is brought into contact with the body.

Examples of the liquid-permeable sheet include air-through, spunbond, chemical bond, or needle punch non-woven fabrics made of fibers of polyethylene, polypropylene, polyester, or the like, and porous synthetic resin sheets. Examples of the liquid-impermeable sheet include synthetic resin films made of resins such as polyethylene, polypropylene, and polyvinyl chloride.

When the water-absorbent resin is used in an adsorbent material, a thin absorbent article having a thickness that is preferably 5 mm or less, more preferably 3 mm or less, for example, can be achieved.

For example, when a water-absorbent resin having a cavity area ratio of 5% or more is selected by the screening method, a water-absorbent resin having both high water-absorbing ability and high water discharge performance can be selected and applied to a water-holding material for soil.

Furthermore, when a water-absorbent resin having a cavity area ratio of 10% or more and a physiological-saline absorption capacity of 40 to 60 g/g is selected, it is possible to provide soil using a large amount of water-absorbent resin.

EXAMPLES

Hereinafter, the present invention will be described in detail with reference to examples and comparative examples. However, the present invention is not limited to the examples.

Water-absorbent resins obtained in the following examples and comparative examples were evaluated using the tests described below. Each of the testing methods for evaluation will be hereinafter described.

<Measurement of Cavity Area Ratio Using X-Ray Computed Tomography>

Particles of the water-absorbent resin were classified in advance with JIS standard sieves. Four particles were randomly selected from particles of the water-absorbent resin on a sieve with a mesh size of 180 µm that passed through a sieve with a mesh size of 600 µm, and these particles were used as resin samples. The resin samples were placed on a sample stage of an X-ray computer tomography apparatus (MicroXCT-400 from Xradia Inc.), and cross-sectional image data were acquired using X-ray computer tomography. Next, for each of the resin samples, shapes at given angles or given horizontal and vertical cross sections were observed using image analysis software (myVGL from Volume Graphics GmbH).

Here, from given cross sections in horizontal directions (x- and y-directions) and a vertical direction (z-direction) with respect to the mounting surface of the sample stage, a horizontal or vertical cross-sectional image having a maximum distance between given two points on the contour of each of the resin samples was selected. Specifically, as shown in the schematic diagram of FIG. 1, for each of the three directions, x-, y-, and z-directions, that are perpendicular to one another, cross-sectional images of a resin sample 11 on the sample stage 10 were acquired first. Subsequently, for each of these directions, one cross-sectional image having the longest particle length w (see FIGS. 1 and 2) of the resin sample (i.e., a cross-sectional image taken in a position where the particle length of the resin sample was the longest) was selected. Then, a cross-sectional image having the longest particle length w of the resin sample of these three cross-sectional images was selected.

More specifically, initially, cross sections (z-x sections) of slices of the resin sample were observed in y-direction while shifting the position in y-direction with respect to the mounting surface of the sample stage, and a z-x cross section having the longest particle length w of the resin sample (see FIGS. 1 and 2) was acquired. Similarly, cross sections (a z-y cross section and an x-y cross section) having the longest particle length w of the resin sample as observed in x- and z-directions were acquired. Then, a cross section having the longest particle length w of the resin sample of these three cross sections was selected.

Next, the cavity area ratio was calculated using this cross-sectional image. By means of general-purpose image processing software (NanoHunter NS2K-Pro/Lt from Nanosystem Corporation), the cross-sectional area of the resin sample (total cross-sectional area of resin portions (A) in the water-absorbent resin) (the area of the filled portions in the schematic diagram of FIG. 2(a)) and the cross-sectional area of the cross section of the resin sample in which cavities are filled (the area of the filled portion in the schematic diagram of FIG. 2(b)) were measured. The cross-sectional area of cavity portions in the resin sample (total cross-sectional area of cavity portions (B) in the water-absorbent resin) was calculated by subtracting the cross-sectional area of the resin sample from the cross-sectional area of the resin sample in which cavities are filled. Then, the cavity area ratio of the resin sample was calculated according to Equation (I) shown below. Using this method, the cavity area ratio of the resin sample was measured for each of the four resin samples, and the average value thereof was determined as the cavity area ratio of the water-absorbent resin.

cavity area ratio [%]={total cross-sectional area $(B)$ of cavity portions in the water-absorbent resin/ (total cross-sectional area $(A)$ of resin portions in the water-absorbent resin+total cross-sectional area $(B)$ of cavity portions in the water-absorbent resin)}×100.    (I)

The conditions for X-ray computer tomography were as follows:
Apparatus: MicroXCT-400 (Xradia Inc.)
X-ray tube voltage: 80 kV
X-ray tube current: 122 µA
Optical lens: 10 times
Irradiation time: 0.8 sec
Pixel size: 2.149 µm
X-ray source-to-sample distance: 29.1533 mm
Detector-to-sample distance: 7.3723 mm
Imaging range: −90° to 90°
Image analyzer: myVGL 2.2 (Volume Graphics GmbH)

<Median Particle Diameter>

JIS standard sieves having mesh sizes of 850 µm, 600 µm, 500 µm, 425 µm, 300 µm, 250 µm, and 150 µm, and a receiving tray were combined in that order from the top.

50 g of the water-absorbent resin was placed on the top sieve of the combined sieves, and shaken for 20 minutes with a Ro-Tap shaker to conduct classification. After the classification, the particle size distribution was determined by calculating the mass of the water-absorbent resin remaining on each sieve as the mass percentage relative to the total mass. With regard to this particle size distribution, the mass percentage of the water-absorbent resin remaining on each sieve was integrated in descending order of particle diameter. Thereby, the relationship between the sieve mesh size and the integrated value of the mass percentage of the water-absorbent resin remaining on each sieve was plotted on logarithmic probability paper. The plots on the probability paper were connected with straight lines, and a particle diameter equivalent to 50% by mass of the integrated mass percentage was determined as the median particle diameter.

<Physiological Saline-Retention Capacity>

500 g of a 0.9% by mass aqueous solution of sodium chloride (physiological saline) was weighed out into a 500-ml beaker, and 2.0±0.001 g of the water-absorbent resin was dispersed therein with stirring using a magnetic stirrer bar (8 mm in diameter×30 mm, without a ring) at 600 rpm, so as not to form unswollen lumps. The dispersion was allowed to stand with stirring for 30 minutes, such that the water-absorbent resin was sufficiently swollen. The dispersion was subsequently poured into a cotton bag (Cottonbroad No. 60, 100 mm in width×200 mm in length), and the top of the cotton bag was closed with a rubber band. Then, the cotton bag was dehydrated for 1 minute using a dehydrator (product number: H-122 from Kokusan Co., Ltd.) set at a centrifugal force of 167 G, and the mass Wa (g) of the dehydrated cotton bag containing the swollen gel was measured. The same procedure was performed without adding the water-absorbent resin, and the mass Wb (g) of the empty cotton bag upon wetting was measured. The physiological saline-retention capacity of the water-absorbent resin was calculated according to the following equation:

Physiological saline-retention capacity (g/g)=[$Wa-Wb$](g)/mass (g) of the water-absorbent resin <Measurement of Physiological Saline-Retention Ratio Under a Load>

The physiological saline-retention ratio under a load was measured in a room adjusted to a temperature of 25° C.±1° C. 250 g of physiological saline adjusted to a temperature of 25° C. in a thermostat was placed in a 500-ml beaker, and 0.9±0.001 g of the water-absorbent resin was dispersed therein with stirring using a magnetic stirrer bar (8 mm in diameter×30 mm, without a ring) at 600 rpm, so as not to form unswollen lumps. The dispersion was allowed to stand with stirring for 60 minutes, such that the water-absorbent resin was sufficiently swollen.

Next, the mass (W0) of a cylinder with an inside diameter of 60 mm and a height of 70 mm, having a 400-mesh stainless steel mesh attached to the bottom, was measured. Then, all contents in the beaker were poured into the cylinder, and the water was drained for 1 minute through a wire gauze with a thickness of 1 mm and a mesh of 1.5 mm. The mass (W1) of the cylinder after draining the water for 1 minute (including the water-absorbent resin after draining the water) was measured. Then, a water-absorption factor of the water-absorbent resin after draining the water for 1 minute was calculated from W0 and W1, according to the following equation.

Water-absorption factor (g/g) after draining the water for 1 minute=$\{[W1-(W0+\text{mass of the water-absorbent resin})]/\text{mass of the water-absorbent resin}\}\times 100$ Next, a weight capable of evenly applying a load of 21 g/cm² was placed on the water-absorbent resin after draining of the water, and the water was again drained for 15 minutes through the wire gauze. The mass (W2) of the cylinder after draining the water under pressure (including the water-absorbent resin after draining the water under pressure) was measured. Then, a water-absorption factor of the water-absorbent resin after draining the water under pressure for 15 minutes was calculated from W2 and W0, according to the following equation:

Water-absorption factor (g/g) after draining the water under pressure for 15 minutes=$\{[W2-(W0+\text{mass of the water-absorbent resin})]/\text{mass of the water-absorbent resin}\}\times 100$.

From the water-absorption factor after draining the water for 1 minute and the water-absorption factor after draining the water under pressure for 15 minutes, the physiological saline-retention ratio under a load was calculated as follows:

Physiological saline-retention ratio under a load (%)={(water-absorption factor after draining the water under pressure for 15 minutes)/(water-absorption factor after draining the water for 1 minute)}×100.

The water-absorbent resin evaluated in the various tests described above was taken as an absorbent article, for example, and the amount of re-wet was evaluated. Hereinafter, a method for evaluating the amount of re-wet in an absorbent article will be described.

<Amount of Re-Wet in Absorbent Article>

(1) Preparation of Artificial Urine 60 g of sodium chloride, 1.8 g of calcium chloride dihydrate, 3.6 g of magnesium chloride hexahydrate, and a suitable amount of distilled water were placed in a 10-L container, and completely dissolved. Next, 0.02 g of polyoxyethylene nonylphenyl ether was added, and then distilled water was added to adjust the mass of the entire aqueous solution to 6000 g. Lastly, the resulting product was colored with a small amount of Blue No. 1 to obtain artificial urine.

(2) Preparation of Water-Absorbent Sheet

A homogenous mixture of 30 parts by mass of an ethylene-vinyl acetate copolymer (EVA; melting point: 95° C.) as an adhesive and 90 parts by mass of the water-absorbent resin was charged into an inlet of a roller-type sprayer (SINTERACE M/C from Hashima Co., Ltd.). Separately, a polypropylene spunbond-melt blown-spunbond (SMS) with a width of 30 cm (a nonwoven fabric hydrophilized with a hydrophilizing agent (weight per unit area: 13 g/m², thickness: 150 μm, polypropylene content: 100%, hydrophilic degree: 16; referred to as "nonwoven fabric A")) was laid over a conveyor in the lower section of the sprayer. Next, the spraying roller and the conveyor in the lower section were operated to uniformly laminate the mixture onto the nonwoven fabric at a weight per unit area of 300 g/m².

The resulting laminate was sandwiched using another nonwoven fabric A, and then these parts were integrated by thermal fusion with a thermal laminator (linear adhesion press HP-600LF from Hashima Co., Ltd.) set at a heating temperature of 130° C. to obtain a water-absorbent sheet.

(3) Preparation of Absorbent Article

The obtained water-absorbent sheet was cut into a rectangular shape having a width of 30 cm and a length of 40 cm, and having a longitudinal direction corresponding to the warp direction (machine direction) of the nonwoven fabric. Next, a polyethylene-polypropylene air-through porous liquid-permeable sheet having the same size as that of the water-absorbent sheet and having a basis weight of 22 g/m² was positioned on an upper surface of the water-absorbent sheet, and a polyethylene liquid-impermeable sheet having the same size and the same basis weight was positioned on a lower surface of the water-absorbent sheet, such that the water-absorbent sheet was sandwiched between these sheets. As a result, an absorbent article was prepared.

(4) Measurement of Amount of Re-Wet in Absorbent Article

Next, the absorbent article was placed on a horizontal stage. A measurement device equipped with a cylinder having an inside diameter of 3 cm through which a liquid was to be added was placed on a central portion of the absorbent article. 50 mL of the artificial urine was added into the cylinder at a time, and the absorbent article was kept as is. At 30 and 60 minutes after the start of the first addition of the artificial urine, this procedure was performed on the same position as the first time. At 120 minutes after the first addition of the test liquid, filter paper measuring 10 cm per side, whose mass had been measured in advance (54 sheets, the total mass (Wd) being about 50 g), was placed near the position on the absorbent article to which the artificial urine was added, and a weight with a mass of 5 kg having a 10 cm×10 cm bottom surface was placed on the filter paper. After the load was applied for 5 minutes, the mass of the filter paper (We (g)) was measured, and the increased mass was determined as the amount of re-wet (g).

<Production of Water-Absorbent Resin>

Example 1

A 2-L cylindrical round-bottomed separable flask having an inside diameter of 110 mm, and equipped with a reflux condenser, a dropping funnel, a nitrogen gas inlet tube, and a stirrer having stirring blades composed of two sets of four inclined paddle blades with a blade diameter of 50 mm was prepared. This flask was charged with 300 g of n-heptane as a hydrocarbon dispersion medium, and then 0.74 g of a sucrose stearate having an HLB of 3 (Ryoto sugar ester S-370 from Mitsubishi-Kagaku Foods Corporation) as a surfactant and 0.74 g of a maleic anhydride-modified ethylene-propylene copolymer (Hi-wax 1105A from Mitsui Chemicals, Inc.) as a polymeric dispersion agent were added thereto. The mixture was heated with stirring to 80° C. to dissolve the surfactant, and then cooled to 50° C.

Separately, 92 g (1.02 mol) of an 80% by mass aqueous solution of acrylic acid was placed in a 500-mL Erlenmeyer flask, and 146.0 g of a 21% by mass aqueous solution of sodium hydroxide was added dropwise with external cooling to accomplish 75 mol % neutralization. Then, 0.092 g of hydroxyethylcellulose (HEC AW-15F from Sumitomo Seika Chemicals Co. Ltd.) as a thickener, 0.11 g (0.00041 mol) of 2,2'-azobis(2-amidinopropane) dihydrochloride as an azo-based compound, and 0.0064 g (0.000037 mol) of ethylene glycol diglycidyl ether as an internal-crosslinking agent were added and dissolved. As a result, an aqueous monomer solution was prepared.

The rotation speed of the stirrer was adjusted to 500 rpm. Then, the aqueous monomer solution prepared as described above was added into the separable flask, and the atmosphere within the system was sufficiently replaced with nitrogen. The flask was subsequently immersed in a water bath at 70° C. and heated to start polymerization. Next, at the time when the temperature within the system had reached a peak temperature (80 to 90° C.) of polymerization, the water bath was adjusted to 80° C., and the reaction mixture was heated for 60 minutes. As a result, first-stage polymerization slurry was obtained.

Separately, 128.8 g (1.43 mol) of an 80% by mass aqueous solution of acrylic acid was placed in another 500-mL Erlenmeyer flask, and 159.0 g of a 27% by mass aqueous solution of sodium hydroxide was added dropwise with external cooling to accomplish 75 mol % neutralization. Then, 0.129 g (0.475 mmol) of 2,2'-azobis(2-amidinopropane) dihydrochloride as an azo-based compound and 0.0116 g (0.067 mmol) of ethylene glycol diglycidyl ether as an internal-crosslinking agent were added and dissolved. As a result, a second-stage aqueous monomer solution was prepared.

The rotation speed of the stirrer was changed to 1000 rpm, and then the atmosphere within the separable flask was cooled. The entire amount of the second-stage aqueous monomer solution was added to the first-stage polymerization slurry, and the atmosphere within the system adjusted to 27° C. was sufficiently replaced with nitrogen. The flask was again immersed in a water bath at 70° C. and heated, and the second-stage polymerization was performed for 30 minutes. After the second-stage polymerization, the reaction mixture in the flask was heated in an oil bath at 125° C. to distill 239 g of water out of the system while refluxing n-heptane by azeotropic distillation of water and n-heptane. Then, 4.42 g (0.51 mmol) of a 2% by mass aqueous solution of ethylene glycol diglycidyl ether as a post-crosslinking agent was added, and the mixture was kept at 80° C. for 120 minutes. Subsequently, n-heptane was evaporated, and the mixture was dried to obtain a resin powder. The resin powder was passed through a sieve with a mesh size of 850 μm to obtain 244.0 g of a water-absorbent resin with a median particle diameter of 400 μm in which spherical particles were aggregated.

Example 2

A 2-L cylindrical round-bottomed separable flask having an inside diameter of 110 mm, and equipped with a reflux condenser, a dropping funnel, a nitrogen gas inlet tube, and a stirrer having stirring blades composed of two sets of four inclined paddle blades with a blade diameter of 50 mm was prepared. This flask was charged with 300 g of n-heptane as a hydrocarbon dispersion medium, and then 0.74 g of a sucrose stearate having an HLB of 3 (Ryoto sugar ester S-370 from Mitsubishi-Kagaku Foods Corporation) as a surfactant and 0.74 g of a maleic anhydride-modified ethylene-propylene copolymer (Hi-wax 1105A from Mitsui Chemicals, Inc.) as a polymeric dispersion agent were added thereto. The mixture was heated with stirring to 80° C. to dissolve the surfactant, and then cooled to 50° C.

Separately, 92 g (1.02 mol) of an 80% by mass aqueous solution of acrylic acid was placed in a 500-mL Erlenmeyer flask, and 146.0 g of a 21% by mass aqueous solution of sodium hydroxide was added dropwise with external cooling to accomplish 75 mol % neutralization. Then, 0.092 g of hydroxyethylcellulose (HEC AW-15F from Sumitomo Seika Chemicals Co. Ltd.) as a thickener, 0.11 g (0.00041 mol) of 2,2'-azobis(2-amidinopropane) dihydrochloride as an azo-based compound, and 0.0064 g (0.000037 mol) of ethylene glycol diglycidyl ether as an internal-crosslinking agent were added and dissolved. As a result, an aqueous monomer solution was prepared.

The rotation speed of the stirrer was adjusted to 600 rpm. Then, the aqueous monomer solution prepared as described above was added into the separable flask, and the atmosphere within the system was sufficiently replaced with nitrogen. The flask was subsequently immersed in a water bath at 70° C. and heated to start polymerization. Next, at the time when the temperature within the system had reached a peak temperature (80 to 90° C.) of polymerization, the water bath was adjusted to 80° C., and the reaction mixture was heated for 60 minutes. As a result, first-stage polymerization slurry was obtained.

Separately, 128.8 g (1.43 mol) of an 80% by mass aqueous solution of acrylic acid was placed in another 500-mL Erlenmeyer flask, and 159.0 g of a 27% by mass aqueous solution of sodium hydroxide was added dropwise with external cooling to accomplish 75 mol % neutralization. Then, 0.129 g (0.475 mmol) of 2,2'-azobis(2-amidinopropane) dihydrochloride as an azo-based compound and 0.0116 g (0.067 mmol) of ethylene glycol diglycidyl ether as an internal-crosslinking agent were added and dissolved. As a result, a second-stage aqueous monomer solution was prepared.

The rotation speed of the stirrer was changed to 1000 rpm, and then the atmosphere within the separable flask was cooled. The entire amount of the second-stage aqueous monomer solution was added to the first-stage polymerization slurry, and the atmosphere within the system adjusted to 27° C. was sufficiently replaced with nitrogen. The flask was again immersed in a water bath at 70° C. and heated, and the second-stage polymerization was performed for 30 minutes. After the second-stage polymerization, the reaction mixture in the flask was heated in an oil bath at 125° C. to distill 244 g of water out of the system while refluxing n-heptane into the system by azeotropic distillation of water and n-heptane. Then, 4.42 g (0.51 mmol) of a 2% by mass aqueous solution of ethylene glycol diglycidyl ether as a post-crosslinking agent was added, and the mixture was kept at 80° C. for 120 minutes. Subsequently, n-heptane was evaporated, and the mixture was dried to obtain a resin powder. The resin powder was passed through a sieve with a mesh size of 850 µm to obtain 243.0 g of a water-absorbent resin with a median particle diameter of 390 µm in which spherical particles were aggregated.

Comparative Example 1

A 2-L cylindrical round-bottomed separable flask having an inside diameter of 110 mm, and equipped with a reflux condenser, a dropping funnel, a nitrogen gas inlet tube, and a stirrer having stirring blades composed of two sets of four inclined paddle blades with a blade diameter of 50 mm was prepared. This flask was charged with 300 g of n-heptane as a hydrocarbon dispersion medium, and then 0.74 g of a sucrose stearate having an HLB of 3 (Ryoto sugar ester S-370 from Mitsubishi-Kagaku Foods Corporation) as a surfactant and 0.74 g of a maleic anhydride-modified ethylene-propylene copolymer (Hi-wax 1105A from Mitsui Chemicals. Inc.) as a polymeric dispersion agent were added thereto. The mixture was heated with stirring to 80° C. to dissolve the surfactant, and then cooled to 50° C.

Separately, 92 g (1.02 mol) of an 80% by mass aqueous solution of acrylic acid was placed in a 500-mL Erlenmeyer flask, and 146.0 g of a 21% by mass aqueous solution of sodium hydroxide was added dropwise with external cooling to accomplish 75 mol % neutralization. Then, 0.092 g of hydroxyethylcellulose (HEC AW-15F from Sumitomo Seika Chemicals Co. Ltd.) as a thickener, 0.11 g (0.00041 mol) of 2,2'-azobis(2-amidinopropane) dihydrochloride as an azo-based compound, and 0.0064 g (0.000037 mol) of ethylene glycol diglycidyl ether as an internal-crosslinking agent were added and dissolved. As a result, an aqueous monomer solution was prepared.

The rotation speed of the stirrer was adjusted to 600 rpm. Then, the aqueous monomer solution prepared as described above was added into the separable flask, and the atmosphere within the system was sufficiently replaced with nitrogen. The flask was subsequently immersed in a water bath at 70° C. and heated to start polymerization. Next, at the time when the temperature within the system had reached a peak temperature (80 to 90° C.) of polymerization, the rotation speed of the stirrer was changed to 1000 rpm, and in an oil bath at 125° C., 23 g of water was distilled out of the system while refluxing n-heptane by azeotropic distillation of water and n-heptane, so that first-stage polymerization slurry was obtained.

Separately, 128.8 g (1.43 mol) of an 80% by mass aqueous solution of acrylic acid was placed in another 500-mL Erlenmeyer flask, and 159.0 g of a 27% by mass aqueous solution of sodium hydroxide was added dropwise with external cooling to accomplish 75 mol % neutralization. Then, 0.11 g (0.00041 mol) of 2,2'-azobis(2-amidinopropane) dihydrochloride as an azo-based compound and 0.0116 g (0.000067 mol) of ethylene glycol diglycidyl ether as an internal-crosslinking agent were added and dissolved. As a result, a second-stage aqueous monomer solution was prepared.

The atmosphere within the separable flask was cooled. Then, the entire amount of the second-stage aqueous monomer solution was added to the first-stage polymerization slurry, and the atmosphere within the system adjusted to 27° C. was sufficiently replaced with nitrogen. The flask was again immersed in a water bath at 70° C. and heated, and the second-stage polymerization was performed for 30 minutes.

After the second-stage polymerization, the reaction mixture in the flask was heated in an oil bath at 125° C. to distill 227 g of water out of the system while refluxing n-heptane into the system by azeotropic distillation of water and n-heptane. Then, 4.42 g (0.51 mmol) of a 2% by mass aqueous solution of ethylene glycol diglycidyl ether as a post-crosslinking agent was added, and the mixture was kept at 80° C. for 120 minutes. Subsequently, n-heptane was evaporated, and the mixture was dried to obtain a resin powder. The resin powder was passed through a sieve with a mesh size of 850 µm to obtain 236.0 g of a water-absorbent resin with a median particle diameter of 380 µm in which spherical particles were aggregated.

Comparative Example 2

A 2-L cylindrical round-bottomed separable flask having an inside diameter of 110 mm, and equipped with a reflux condenser, a dropping funnel, a nitrogen gas inlet tube, and a stirrer having stirring blades composed of two sets of four inclined paddle blades with a blade diameter of 50 mm was prepared. This flask was charged with 300 g of n-heptane as a hydrocarbon dispersion medium, and then 0.74 g of a sucrose stearate having an HLB of 3 (Ryoto sugar ester S-370 from Mitsubishi-Kagaku Foods Corporation) as a surfactant and 0.74 g of a maleic anhydride-modified ethylene-propylene copolymer (Hi-wax 1105A from Mitsui Chemicals, Inc.) as a polymeric dispersion agent were added thereto. The mixture was heated with stirring to 80° C. to dissolve the surfactant, and then cooled to 50° C.

Separately, 92 g (1.02 mol) of an 80% by mass aqueous solution of acrylic acid was placed in a 500-mL Erlenmeyer flask, and 146.0 g of a 21% by mass aqueous solution of sodium hydroxide was added dropwise with external cooling to accomplish 75 mol % neutralization. Then, 0.092 g of hydroxyethylcellulose (HEC AW-15F from Sumitomo Seika Chemicals Co. Ltd.) as a thickener, 0.11 g (0.00041 mol) of 2,2'-azobis(2-amidinopropane) dihydrochloride as an azo-based compound, and 0.0064 g (0.000037 mol) of ethylene glycol diglycidyl ether as an internal-crosslinking agent were added and dissolved. As a result, an aqueous monomer solution was prepared.

The rotation speed of the stirrer was adjusted to 500 rpm. Then, the aqueous monomer solution prepared as described above was added into the separable flask, and the atmosphere within the system was sufficiently replaced with nitrogen. The flask was subsequently immersed in a water bath at 70° C. and heated to start polymerization. Next, at the time when the temperature within the system had reached a peak temperature (80 to 90° C.) of polymerization, the rotation speed of the stirrer was changed to 1000 rpm, and in an oil bath at 125° C., 92 g of water was distilled out of the system while refluxing n-heptane into the system by azeotropic distillation of water and n-heptane, so that first-stage polymerization slurry was obtained.

Separately, 128.8 g (1.43 mol) of an 80% by mass aqueous solution of acrylic acid was placed in another 500-mL Erlenmeyer flask, and 159.0 g of a 27% by mass aqueous solution of sodium hydroxide was added dropwise with external cooling to accomplish 75 mol % neutralization. Then, 0.11 g (0.00041 mol) of 2,2'-azobis(2-amidinopropane) dihydrochloride as an azo-based compound and 0.0116 g (0.000067 mol) of ethylene glycol diglycidyl ether as an internal-crosslinking agent were added and dissolved. As a result, a second-stage aqueous monomer solution was prepared.

The atmosphere within the separable flask was cooled. Then, the entire amount of the second-stage aqueous monomer solution was added to the first-stage polymerization slurry, and the atmosphere within the system adjusted to 27° C. was sufficiently replaced with nitrogen. The flask was again immersed in a water bath at 70° C. and heated, and the second-stage polymerization was performed for 30 minutes.

After the second-stage polymerization, the reaction mixture in the flask was heated in an oil bath at 125° C. to distill 168 g of water out of the system while refluxing n-heptane into the system by azeotropic distillation of water and n-heptane. Then, 4.42 g (0.51 mmol) of a 2% by mass aqueous solution of ethylene glycol diglycidyl ether as a post-crosslinking agent was added, and the mixture was kept at 80° C. for 120 minutes. Subsequently, n-heptane was evaporated, and the mixture was dried to obtain a resin powder. The resin powder was passed through a sieve with a mesh size of 850 μm to obtain 238.0 g of a water-absorbent resin with a median particle diameter of 370 μm in which spherical particles were aggregated.

Table 1 shows the results of evaluation of the water-absorbent resins produced in the examples and comparative examples as well as absorbent articles obtained with these water-absorbent resins, using the testing methods for evaluation described above.

TABLE 1

|  | Cavity area ratio (%) | Physiological saline-retention capacity (g/g) | Physiological saline-retention ratio under load (%) | Amount of re-wet in absorbent article (g) |
|---|---|---|---|---|
| Example 1 | 3 | 42 | 76 | 0.8 |
| Example 2 | 6 | 45 | 77 | 0.6 |
| Comparative Example 1 | 11 | 40 | 69 | 3.7 |
| Comparative Example 2 | 11 | 46 | 71 | 3.3 |

As is clear from the results shown in Table 1, the water-absorbent resins of Examples 1 and 2 evaluated to have a ratio of the area of cavity portions (cavity area ratio) of 10% or less as calculated according to Equation (I) above by the non-destructive method for evaluating a structure of a water-absorbent resin of the present invention each exhibit a high physiological saline-retention ratio under a load, and effectively reduce the amount of re-wet when used as a water-absorbent sheet. That is, it is evaluated that by setting the cavity area ratio of the water-absorbent resin to 10% or less, a water-absorbent resin that exhibits a high liquid-retention capacity under a load and has a small amount of re-wet can be achieved and, for example, the water-absorbent resin can be suitably used for an absorbent material having a small proportion of hydrophilic fibers.

DESCRIPTION OF REFERENCE SIGNS

10: Sample stage
11: Water-absorbent resin
w: Particle length

The invention claimed is:
1. A non-destructive method for evaluating a structure of a crosslinked water-absorbent resin through X-ray computer tomography, the method comprising:
    placing the crosslinked water-absorbent resin to be evaluated on a sample stage of an X-ray computer tomography apparatus;
    performing X-ray computer tomography on the crosslinked water-absorbent resin by using the X-ray computer tomography apparatus to acquire tomographic image data of the crosslinked water-absorbent resin;
    analyzing the tomographic image data by using image analysis software to obtain a cross-sectional image of the crosslinked water-absorbent resin;
    using image processing software to measure a total cross-sectional area (A) of resin portions in the crosslinked water-absorbent resin and a total cross-sectional area (B) of cavity portions in the crosslinked water-absorbent resin from the cross-sectional image of the crosslinked water-absorbent resin; and
    calculating a cavity area ratio of the crosslinked water-absorbent resin by Evaluation (I):

cavity area ratio [%]={total cross-sectional area (B) of cavity portions in the crosslinked water-absorbent resin/(total cross-sectional area (A) of resin portions in the crosslinked water-absorbent resin+total cross-sectional area (B) of cavity portions in the crosslinked water-absorbent resin)}×100.   (I)

2. The non-destructive method for evaluating a structure of a crosslinked water-absorbent resin, according to claim 1, wherein the shape of the crosslinked water-absorbent resin to be evaluated is a granular shape, a substantially spherical shape, a crushed indefinite shape, a flat shape, a shape in which particles having a substantially spherical shape are aggregated, or a shape in which particles having a crushed indefinite shape are aggregated.

3. A method for screening a crosslinked water-absorbent resin used for an absorbent material, comprising:
    nondestructively evaluating a structure of the crosslinked water-absorbent resin by the method of claim 1; and
    selecting the crosslinked water-absorbent resin to be used for the absorbent material.

4. A non-destructive method for evaluating a structure of a crosslinked water-absorbent resin through X-ray computer tomography, the method comprising:

placing the crosslinked water-absorbent resin to be evaluated on a sample stage of an X-ray computer tomography apparatus;

performing X-ray computer tomography on the crosslinked water-absorbent resin by using the X-ray computer tomography apparatus to acquire tomographic image data of the crosslinked water-absorbent resin;

analyzing the tomographic image data by using image analysis software to obtain a cross-sectional image of the crosslinked water-absorbent resin;

using image processing software to measure a total cross-sectional area (A) of resin portions in the crosslinked water-absorbent resin and a cross-sectional area (C) of a cross section of the crosslinked water-absorbent resin in which cavities are filled from the cross-sectional image of the crosslinked water-absorbent resin;

subtracting the total cross-sectional area (A) from the cross-sectional area (C) to calculate the total cross-sectional area (B) of cavity portions in the crosslinked water-absorbent resin; and calculating a cavity area ratio of the crosslinked water-absorbent resin by Evaluation (I):

cavity area ratio [%]={total cross-sectional area (*B*) of cavity portions in the crosslinked water-absorbent resin/(total cross-sectional area (*A*) of resin portions in the crosslinked water-absorbent resin+total cross-sectional area (*B*) of cavity portions in the crosslinked water-absorbent resin)}×100.

5. The non-destructive method for evaluating a structure of a crosslinked water-absorbent resin, according to claim 4, wherein the shape of the crosslinked water-absorbent resin to be evaluated is a granular shape, a substantially spherical shape, a crushed indefinite shape, a flat shape, a shape in which particles having a substantially spherical shape are aggregated, or a shape in which particles having a crushed indefinite shape are aggregated.

6. A method for screening a crosslinked water-absorbent resin used for an absorbent material, comprising:

nondestructively evaluating a structure of the crosslinked water-absorbent resin by the method of claim 4; and selecting the crosslinked water-absorbent resin to be used for the absorbent material.

* * * * *